US012576199B2

(12) United States Patent
Marra

(10) Patent No.: US 12,576,199 B2
(45) Date of Patent: Mar. 17, 2026

(54) FLOWMETER FOR PROPORTIONING WATER IN DIALYSIS SYSTEM

(71) Applicant: Bellco S.r.l., Mirandola (IT)

(72) Inventor: Antonio Giuseppe Marra, Mirandola (IT)

(73) Assignee: Bellco S.r.l., Mirandola (IT)

( * ) Notice: Subject to any disclaimer, the term of this patent is extended or adjusted under 35 U.S.C. 154(b) by 1072 days.

(21) Appl. No.: 17/512,100

(22) Filed: Oct. 27, 2021

(65) Prior Publication Data

US 2022/0126009 A1     Apr. 28, 2022

(30) Foreign Application Priority Data

Oct. 27, 2020    (EP) ...................................... 20203997

(51) Int. Cl.
*A61M 1/36*         (2006.01)
*A61M 1/16*         (2006.01)
(Continued)

(52) U.S. Cl.
CPC ........ *A61M 1/3626* (2013.01); *A61M 1/1601* (2014.02); *A61M 1/1607* (2014.02); *A61M 1/1615* (2014.02); *A61M 1/1654* (2013.01); *A61M 1/1658* (2013.01); *A61M 1/1666* (2014.02); *A61M 1/282* (2014.02); *A61M 1/287* (2013.01); *G01D 21/02* (2013.01); *G01P 5/245* (2013.01); *G01P 5/26* (2013.01); A61M 1/28 (2013.01); A61M 2205/3306 (2013.01); A61M 2205/3334 (2013.01);
(Continued)

(58) Field of Classification Search
CPC .............. A61M 1/1601; A61M 1/1607; A61M 1/1615; A61M 1/1654; A61M 1/1658; A61M 1/1666; A61M 1/28; A61M 1/282; A61M 1/287; A61M 1/3626; A61M 2205/3306; A61M 2205/3334; A61M 2205/3375; A61M 2205/50; A61M 2205/583; G01P 5/245; G01P 5/26; G01D 21/02
See application file for complete search history.

(56) References Cited

U.S. PATENT DOCUMENTS 3,946,731 A * 3/1976 Lichtenstein ......... A61M 1/155
210/90
5,895,571 A * 4/1999 Utterberg ............ A61M 1/3644
210/252

(Continued)

*Primary Examiner* — John Kim

(57) ABSTRACT

A system includes a fluid source storing a fluid and a fluid line coupled to the fluid source and configured to pass the fluid therethrough. The system includes a bubble detector coupled to the fluid line downstream of the fluid source, the bubble detector configured to detect bubbles present in the fluid and to generate a bubble detection signal. The system also includes a valve coupled to the fluid line downstream of the fluid source, the valve configured to switch between a first configuration and a second configuration, where in the first configuration the valve directs the fluid through the fluid line and in the second configuration the valve directs the fluid through a drain line. The system further includes a controller coupled to the bubble detector and the valve, the controller configured to receive the bubble detection signal and to control the valve based on the bubble detection signal.

13 Claims, 2 Drawing Sheets

(51) Int. Cl.

| | | |
|---|---|---|
| *A61M 1/28* | (2006.01) | |
| *G01D 21/02* | (2006.01) | |
| *G01P 5/24* | (2006.01) | |
| *G01P 5/26* | (2006.01) | |

(52) U.S. Cl.
CPC . *A61M 2205/3375* (2013.01); *A61M 2205/50* (2013.01); *A61M 2205/583* (2013.01)

(56) References Cited

U.S. PATENT DOCUMENTS

| | | | |
|---|---|---|---|
| 5,951,870 A | 9/1999 | Utterberg | |
| 6,044,691 A | 4/2000 | Kenley et al. | |
| 6,066,261 A | 5/2000 | Spickermann | |
| 6,077,443 A | 6/2000 | Goldau | |
| 6,106,776 A | 8/2000 | Borovetz et al. | |
| 6,114,466 A | 9/2000 | Davankov et al. | |
| 6,126,831 A | 10/2000 | Goldau et al. | |
| 6,133,393 A | 10/2000 | Davankov et al. | |
| 6,138,517 A | 10/2000 | Laursen et al. | |
| 6,159,377 A | 12/2000 | Davankov et al. | |
| 6,200,289 B1 | 3/2001 | Hochman et al. | |
| 6,217,826 B1 | 4/2001 | Reeder et al. | |
| 6,221,040 B1 | 4/2001 | Kleinekofort | |
| 6,228,262 B1 | 5/2001 | Shin et al. | |
| 6,241,945 B1 | 6/2001 | Owen | |
| 6,248,087 B1 | 6/2001 | Spears et al. | |
| 6,306,346 B1 | 10/2001 | Lindsay | |
| 6,325,774 B1 | 12/2001 | Bene et al. | |
| 6,344,139 B1 | 2/2002 | Utterberg | |
| 6,348,152 B1 | 2/2002 | Kawahara et al. | |
| 6,387,324 B1 | 5/2002 | Patterson et al. | |
| 6,395,180 B2 | 5/2002 | Chioini et al. | |
| 6,409,024 B1 | 6/2002 | Nakashima et al. | |
| 6,432,309 B1 | 8/2002 | Fuke et al. | |
| 6,468,427 B1 | 10/2002 | Frey | |
| 6,500,151 B1 | 12/2002 | Cobb et al. | |
| 6,503,451 B2 | 1/2003 | Ikeda et al. | |
| 6,519,569 B1 | 2/2003 | White et al. | |
| 6,526,357 B1 | 2/2003 | Soussan et al. | |
| 6,537,240 B2 | 3/2003 | Cavicchioli et al. | |
| 6,555,059 B1 | 4/2003 | Myrick et al. | |
| 6,572,576 B2 | 6/2003 | Brugger et al. | |
| 6,576,191 B1 | 6/2003 | Myrick et al. | |
| 6,582,387 B2 | 6/2003 | Derek et al. | |
| 6,582,811 B1 | 6/2003 | Davankov et al. | |
| 6,585,675 B1 | 7/2003 | O'Mahony et al. | |
| 6,592,551 B1 | 7/2003 | Cobb | |
| 6,595,942 B2 | 7/2003 | Kleinekofort | |
| 6,601,432 B1 | 8/2003 | Ericson et al. | |
| 6,602,424 B1 | 8/2003 | Kramer et al. | |
| 6,602,468 B2 | 8/2003 | Patterson et al. | |
| 6,605,218 B2 | 8/2003 | Kozawa et al. | |
| 6,607,697 B1 | 8/2003 | Muller | |
| 6,613,280 B2 | 9/2003 | Myrick et al. | |
| 6,622,542 B2 | 9/2003 | Derek et al. | |
| 6,623,443 B1 | 9/2003 | Polaschegg | |
| 6,626,355 B2 | 9/2003 | Sasse et al. | |
| 6,627,164 B1 | 9/2003 | Wong | |
| 6,632,359 B1 | 10/2003 | Uezumi et al. | |
| 6,638,710 B2 | 10/2003 | Leinenbach et al. | |
| 6,640,611 B2 | 11/2003 | Ericson et al. | |
| 6,648,845 B1 | 11/2003 | Gotch et al. | |
| 6,653,841 B1 | 11/2003 | Koerdt et al. | |
| 6,673,314 B1 | 1/2004 | Burbank et al. | |
| 6,676,621 B1 | 1/2004 | Menninger | |
| 6,682,698 B2 | 1/2004 | Chambers et al. | |
| 6,685,450 B2 | 2/2004 | Bandis et al. | |
| 6,689,083 B1 | 2/2004 | Gelfand et al. | |
| 6,691,040 B2 | 2/2004 | Bosetto et al. | |
| 6,691,047 B1 | 2/2004 | Fredericks | |
| 6,712,978 B2 | 3/2004 | Leinenbach et al. | |
| 6,723,284 B1 | 4/2004 | Reeder et al. | |
| 6,726,647 B1 | 4/2004 | Sternby et al. | |
| 6,730,266 B2 | 5/2004 | Matson et al. | |
| 6,738,052 B1 | 5/2004 | Manke et al. | |
| 6,759,008 B1 | 7/2004 | Patterson et al. | |
| 6,767,333 B1 | 7/2004 | Muller et al. | |
| 6,773,412 B2 | 8/2004 | O'Mahony et al. | |
| 6,775,577 B2 | 8/2004 | Crnkovich et al. | |
| 6,786,885 B2 | 9/2004 | Hochman et al. | |
| 6,796,955 B2 | 9/2004 | O'Mahony et al. | |
| 6,804,991 B2 | 10/2004 | Balschat et al. | |
| 6,811,707 B2 | 11/2004 | Rovatti et al. | |
| 6,811,750 B2 | 11/2004 | Patterson et al. | |
| 6,818,196 B2 | 11/2004 | Wong | |
| 6,821,432 B2 | 11/2004 | Metzner | |
| 6,830,693 B2 | 12/2004 | Govoni et al. | |
| 6,843,099 B2 | 1/2005 | Derek et al. | |
| 6,846,161 B2 | 1/2005 | Kline et al. | |
| 6,849,235 B2 | 2/2005 | Myrick et al. | |
| 6,854,620 B2 | 2/2005 | Ramey | |
| 6,855,291 B2 | 2/2005 | Patterson et al. | |
| 6,860,866 B1 | 3/2005 | Graf et al. | |
| 6,861,266 B1 | 3/2005 | Sternby | |
| 6,868,309 B1 | 3/2005 | Begelman | |
| 6,877,713 B1 | 4/2005 | Gray et al. | |
| 6,880,034 B2 | 4/2005 | Manke et al. | |
| 6,881,344 B2 | 4/2005 | Vasta et al. | |
| 6,887,216 B2 | 5/2005 | Hochman et al. | |
| 6,890,315 B1 | 5/2005 | Levin et al. | |
| 6,890,482 B2 | 5/2005 | Divino, Jr. et al. | |
| 6,899,847 B2 | 5/2005 | Myrick et al. | |
| 6,908,546 B2 | 6/2005 | Smith | |
| 6,917,828 B2 | 7/2005 | Fukuda | |
| 6,923,782 B2 | 8/2005 | O'Mahony et al. | |
| 6,929,619 B2 | 8/2005 | Fago et al. | |
| 6,929,751 B2 | 8/2005 | Bowman, Jr. et al. | |
| 6,935,560 B2 | 8/2005 | Andreasson et al. | |
| 6,936,221 B1 | 8/2005 | Divino, Jr. et al. | |
| 6,936,222 B2 | 8/2005 | Mortensen et al. | |
| 6,939,111 B2 | 9/2005 | Huitt et al. | |
| 6,939,468 B2 | 9/2005 | Wang et al. | |
| 6,945,954 B2 | 9/2005 | Hochman et al. | |
| 6,949,214 B2 | 9/2005 | Frey | |
| 6,952,963 B2 | 10/2005 | Delnevo | |
| 6,960,328 B2 | 11/2005 | Bortun et al. | |
| 6,966,979 B2 | 11/2005 | Pedrazzi | |
| 6,994,811 B2 | 2/2006 | Kools | |
| 7,001,353 B2 | 2/2006 | Bosetto et al. | |
| 7,004,924 B1 | 2/2006 | Brugger et al. | |
| 7,011,761 B2 | 3/2006 | Muller | |
| 7,013,727 B2 | 3/2006 | Delnevo | |
| 7,014,765 B2 | 3/2006 | Dannenmaier | |
| 7,022,284 B2 | 4/2006 | Brian et al. | |
| 7,025,226 B2 | 4/2006 | Ramey | |
| 7,033,498 B2 | 4/2006 | Wong | |
| 7,033,539 B2 | 4/2006 | Krensky et al. | |
| 7,072,710 B2 | 7/2006 | Chamney | |
| 7,077,819 B1 | 7/2006 | Goldau et al. | |
| 7,077,956 B2 | 7/2006 | Rovatti | |
| 7,087,033 B2 | 8/2006 | Brugger et al. | |
| 7,087,168 B2 | 8/2006 | Oishi et al. | |
| 7,087,269 B2 | 8/2006 | Lee et al. | |
| 7,097,630 B2 | 8/2006 | Gotch et al. | |
| 7,125,493 B2 | 10/2006 | Wang et al. | |
| 7,131,956 B1 | 11/2006 | Pirazzoli et al. | |
| 7,131,957 B2 | 11/2006 | Muller et al. | |
| 7,135,156 B2 | 11/2006 | Hai et al. | |
| 7,140,542 B2 | 11/2006 | Andreasson et al. | |
| 7,147,616 B2 | 12/2006 | Pedrazzi et al. | |
| 7,153,285 B2 | 12/2006 | Lauman et al. | |
| 7,154,378 B1 | 12/2006 | Ertas et al. | |
| 7,166,084 B2 | 1/2007 | Utterberg | |
| 7,169,352 B1 | 1/2007 | Felt et al. | |
| 7,170,591 B2 | 1/2007 | Ohishi et al. | |
| 7,172,569 B2 | 2/2007 | Kleinekofort | |
| 7,172,570 B2 | 2/2007 | Cavalcanti et al. | |
| 7,175,081 B2 | 2/2007 | Andreasson et al. | |
| 7,175,809 B2 | 2/2007 | Gelfand et al. | |
| 7,182,256 B2 | 2/2007 | Andreasson et al. | |
| 7,186,342 B2 | 3/2007 | Pirazzoli et al. | |
| 7,186,420 B2 | 3/2007 | Chang et al. | |
| 7,186,966 B2 | 3/2007 | Ai-Ali | |

(56)                    References Cited

U.S. PATENT DOCUMENTS

| | | |
|---|---|---|
| 7,232,424 B2 | 6/2007 | Boyne-Aitken |
| 7,241,272 B2 | 7/2007 | Karoor et al. |
| 7,252,767 B2 | 8/2007 | Bortun et al. |
| 7,258,914 B2 | 8/2007 | Morikawa et al. |
| 7,299,981 B2 | 11/2007 | Hickle et al. |
| 7,303,540 B2 | 12/2007 | O'Mahony et al. |
| 7,311,689 B2 | 12/2007 | Levin et al. |
| 7,341,568 B2 | 3/2008 | Zhang |
| 7,347,837 B2 | 3/2008 | Azzolini |
| 7,381,195 B2 | 6/2008 | Mori et al. |
| 7,393,337 B2 | 7/2008 | Tonelli et al. |
| 7,399,289 B2 | 7/2008 | Gelfand et al. |
| 7,420,660 B2 | 9/2008 | Muller |
| 7,422,570 B2 | 9/2008 | Gerlach et al. |
| 7,442,302 B2 | 10/2008 | Mabuchi et al. |
| 7,462,161 B2 | 12/2008 | O'Mahony et al. |
| 7,488,447 B2 | 2/2009 | Sternby |
| 7,494,590 B2 | 2/2009 | Felding et al. |
| 7,540,851 B2 | 6/2009 | O'Mahony et al. |
| 7,563,240 B2 | 7/2009 | Gross et al. |
| 7,563,376 B2 | 7/2009 | Oishi |
| 7,566,432 B2 | 7/2009 | Wong |
| 7,575,562 B2 | 8/2009 | Oishi et al. |
| 7,585,286 B2 | 9/2009 | O'Mahony et al. |
| 7,592,184 B2 | 9/2009 | Khalil et al. |
| 7,608,060 B2 | 10/2009 | Gillespie, Jr. et al. |
| 7,615,158 B2 | 11/2009 | Sternby et al. |
| 7,622,043 B2 | 11/2009 | Sawada et al. |
| 7,635,349 B2 | 12/2009 | Tribe et al. |
| 7,638,052 B2 | 12/2009 | Mabuchi et al. |
| 7,639,136 B1 | 12/2009 | Wass et al. |
| 7,648,474 B2 | 1/2010 | Paolini et al. |
| 7,648,476 B2 | 1/2010 | Bock et al. |
| 7,648,477 B2 | 1/2010 | Vinci et al. |
| 7,661,293 B2 | 2/2010 | Dam |
| 7,694,565 B2 | 4/2010 | Koerdt et al. |
| 7,699,992 B2 | 4/2010 | Sternby |
| 7,731,689 B2 | 6/2010 | Prisco et al. |
| 7,736,507 B2 | 6/2010 | Wong |
| 7,748,275 B2 | 7/2010 | Kouda et al. |
| 7,749,184 B2 | 7/2010 | Cavalcanti et al. |
| 7,749,435 B2 | 7/2010 | Ogihara et al. |
| 7,751,043 B2 | 7/2010 | Scarpaci et al. |
| 7,758,532 B2 | 7/2010 | Mori et al. |
| 7,766,863 B2 | 8/2010 | Gillespie, Jr. et al. |
| 7,771,379 B2 | 8/2010 | Treu |
| 7,776,219 B2 | 8/2010 | Brugger et al. |
| 7,780,618 B2 | 8/2010 | Felt et al. |
| 7,790,113 B2 | 9/2010 | Putnam et al. |
| 7,794,419 B2 | 9/2010 | Paolini et al. |
| 7,815,809 B2 | 10/2010 | Jansson et al. |
| 7,823,287 B2 | 11/2010 | Gerlach et al. |
| 7,824,354 B2 | 11/2010 | Vinci et al. |
| 7,837,042 B2 | 11/2010 | Yokota et al. |
| 7,854,726 B2 | 12/2010 | Fago et al. |
| 7,857,976 B2 | 12/2010 | Bissler et al. |
| 7,862,530 B2 | 1/2011 | Callan et al. |
| 7,878,783 B2 | 2/2011 | Kunz |
| 7,896,842 B2 | 3/2011 | Palmroos et al. |
| 7,905,853 B2 | 3/2011 | Chapman et al. |
| 7,905,855 B2 | 3/2011 | Childers |
| 7,906,093 B2 | 3/2011 | Wong |
| 7,911,353 B2 | 3/2011 | Bedingfield |
| 7,922,007 B2 | 4/2011 | Mabuchi et al. |
| 7,922,899 B2 | 4/2011 | Vasta et al. |
| 7,935,071 B2 | 5/2011 | Levin et al. |
| 7,935,072 B2 | 5/2011 | Tonelli et al. |
| 7,938,792 B2 | 5/2011 | Roger et al. |
| 7,938,967 B2 | 5/2011 | Folden et al. |
| 7,955,289 B2 | 6/2011 | O'Mahony et al. |
| 7,955,291 B2 | 6/2011 | Sternby |
| 7,959,196 B2 | 6/2011 | Dale |
| 7,959,808 B2 | 6/2011 | Yeager et al. |
| 7,981,280 B2 | 7/2011 | Carr et al. |
| 7,985,196 B2 | 7/2011 | Kopperschmidt et al. |
| 7,988,768 B2 | 8/2011 | Yardimci et al. |
| 7,988,854 B2 | 8/2011 | Tsukamoto |
| 7,990,272 B2 | 8/2011 | Wass et al. |
| 7,993,297 B2 | 8/2011 | Vinci et al. |
| 8,012,114 B2 | 9/2011 | Daniel et al. |
| 8,034,161 B2 | 10/2011 | Gura et al. |
| 8,035,517 B2 | 10/2011 | Gibson |
| 8,038,886 B2 | 10/2011 | Folden et al. |
| 8,043,076 B2 | 10/2011 | Kopperschmidt |
| 8,051,991 B2 | 11/2011 | Krause et al. |
| 8,066,658 B2 | 11/2011 | Karoor et al. |
| 8,070,707 B2 | 12/2011 | Gelfand et al. |
| 8,075,509 B2 | 12/2011 | Molducci et al. |
| 8,078,333 B2 | 12/2011 | Kienman et al. |
| 8,080,161 B2 | 12/2011 | Ding et al. |
| 8,087,702 B2 | 1/2012 | Schmidt |
| 8,088,090 B2 | 1/2012 | Felt et al. |
| 8,091,407 B2 | 1/2012 | Schneider et al. |
| 8,095,390 B2 | 1/2012 | Bluemler et al. |
| 8,104,348 B2 | 1/2012 | Balschat et al. |
| 8,104,624 B2 | 1/2012 | Chidambaran et al. |
| 8,105,260 B2 | 1/2012 | Tonelli et al. |
| 8,111,159 B2 | 2/2012 | Andreasson et al. |
| 8,136,675 B2 | 3/2012 | Buck et al. |
| 8,137,553 B2 | 3/2012 | Fulkerson et al. |
| 8,140,274 B2 | 3/2012 | Gagel et al. |
| 8,178,040 B2 | 5/2012 | Brauer |
| 8,182,691 B2 | 5/2012 | Stahl |
| 8,197,432 B2 | 6/2012 | O'Mahony et al. |
| 8,197,745 B1 | 6/2012 | Buck et al. |
| 8,202,428 B2 | 6/2012 | Heilmann et al. |
| 8,202,503 B2 | 6/2012 | Putnam et al. |
| 8,210,049 B2 | 7/2012 | Brugger |
| 8,219,982 B2 | 7/2012 | Harkanyi et al. |
| 8,220,643 B2 | 7/2012 | Eisen |
| 8,240,636 B2 | 8/2012 | Smith |
| 8,246,564 B2 | 8/2012 | Myrick et al. |
| 8,287,736 B2 | 10/2012 | Roncadi et al. |
| 8,298,427 B2 | 10/2012 | Ficheux et al. |
| 8,314,740 B2 | 11/2012 | Blumberg, Jr. |
| 8,315,654 B2 | 11/2012 | Balschat et al. |
| 8,315,885 B2 | 11/2012 | Krogh et al. |
| 8,317,168 B2 | 11/2012 | Murakami |
| 8,317,499 B2 | 11/2012 | Ibragimov |
| 8,317,738 B2 | 11/2012 | Ishida et al. |
| 8,325,045 B2 | 12/2012 | Dattolo et al. |
| 8,328,749 B2 | 12/2012 | Murakami et al. |
| 8,333,724 B2 | 12/2012 | Barrett et al. |
| 8,343,085 B2 | 1/2013 | Toyoda et al. |
| 8,350,195 B2 | 1/2013 | Hedmann et al. |
| 8,353,870 B2 | 1/2013 | Levin et al. |
| 8,361,023 B2 | 1/2013 | Bedingfield |
| 8,394,046 B2 | 3/2013 | Nuernberger et al. |
| 8,394,321 B2 | 3/2013 | Franzoni et al. |
| 8,398,858 B2 | 3/2013 | Kashefi-Khorasani et al. |
| 8,400,298 B2 | 3/2013 | Rada |
| 8,409,445 B2 | 4/2013 | Levin et al. |
| 8,409,502 B2 | 4/2013 | Mortensen et al. |
| 8,409,864 B2 | 4/2013 | Ash |
| 8,425,767 B2 | 4/2013 | Fava et al. |
| 8,430,834 B2 | 4/2013 | Kopperschmidt |
| 8,432,547 B2 | 4/2013 | Scarpaci et al. |
| 8,449,487 B2 | 5/2013 | Hovland et al. |
| 8,459,543 B2 | 6/2013 | Devergne et al. |
| 8,465,446 B2 | 6/2013 | Chapman et al. |
| 8,480,609 B2 | 7/2013 | Fava et al. |
| 8,485,998 B2 | 7/2013 | Moll et al. |
| 8,486,021 B2 | 7/2013 | Hoshide et al. |
| 8,496,824 B2 | 7/2013 | Remkes et al. |
| 8,496,874 B2 | 7/2013 | Gellman et al. |
| 8,497,107 B2 | 7/2013 | Merchant |
| 8,512,271 B2 | 8/2013 | Moissl et al. |
| 8,512,554 B2 | 8/2013 | Yu et al. |
| 8,512,564 B2 | 8/2013 | Bene et al. |
| 8,518,247 B2 | 8/2013 | Akita et al. |
| 8,518,326 B2 | 8/2013 | Brady et al. |
| 8,529,491 B2 | 9/2013 | Beiriger |
| 8,539,573 B2 | 9/2013 | Newlin et al. |
| 8,545,425 B2 | 10/2013 | Lundtveit et al. |

(56) References Cited

U.S. PATENT DOCUMENTS

| | | | |
|---|---|---|---|
| 8,558,964 B2 | 10/2013 | Bedingfield |
| 8,560,510 B2 | 10/2013 | Brueggerhoff et al. |
| 8,562,834 B2 | 10/2013 | Kamen et al. |
| 8,562,876 B2 | 10/2013 | Sternberg |
| 8,568,595 B2 | 10/2013 | Castellarnau |
| 8,574,309 B2 | 11/2013 | Galea et al. |
| 8,585,907 B2 | 11/2013 | Raiford et al. |
| 8,585,968 B2 | 11/2013 | Morley et al. |
| 8,596,467 B2 | 12/2013 | Krause et al. |
| 8,597,190 B2 | 12/2013 | Rule et al. |
| 8,597,227 B2 | 12/2013 | Childers et al. |
| 8,597,505 B2 | 12/2013 | Fulkerson et al. |
| 8,603,021 B2 | 12/2013 | Levin et al. |
| 8,608,658 B2 | 12/2013 | Burbank et al. |
| 8,609,022 B2 | 12/2013 | Nakao et al. |
| 8,610,577 B2 | 12/2013 | Blumberg, Jr. |
| 8,617,393 B2 | 12/2013 | Remkes et al. |
| 8,625,100 B2 | 1/2014 | Hanko |
| 8,640,887 B2 | 2/2014 | Wong |
| 8,641,615 B2 | 2/2014 | Burbank et al. |
| 8,641,655 B2 | 2/2014 | Rambod et al. |
| 8,647,410 B2 | 2/2014 | Borenstein et al. |
| 8,657,775 B2 | 2/2014 | Hutchison et al. |
| 8,663,372 B2 | 3/2014 | Romdhane et al. |
| 8,672,145 B2 | 3/2014 | Eisen |
| 8,679,348 B2 | 3/2014 | Burbank et al. |
| 8,684,927 B2 | 4/2014 | Basaglia |
| 8,685,320 B2 | 4/2014 | Ogihara et al. |
| 8,687,003 B2 | 4/2014 | Dalesch et al. |
| 8,733,559 B2 | 5/2014 | Wong |
| 8,741,147 B2 | 6/2014 | Bene et al. |
| 8,747,342 B2 | 6/2014 | Caleffi et al. |
| 8,747,742 B2 | 6/2014 | Kawamura et al. |
| 8,748,538 B2 | 6/2014 | Krause et al. |
| 8,764,981 B2 | 7/2014 | Ding et al. |
| 8,764,987 B2 | 7/2014 | Gross et al. |
| 8,769,625 B2 | 7/2014 | Wang et al. |
| 8,771,215 B2 | 7/2014 | Tonelli et al. |
| 8,771,516 B2 | 7/2014 | Krause et al. |
| 8,775,196 B2 | 7/2014 | Simpson et al. |
| 8,784,668 B2 | 7/2014 | Beiriger |
| 8,803,044 B2 | 8/2014 | Kienman et al. |
| 8,813,769 B2 | 8/2014 | Gastauer et al. |
| 8,814,830 B2 | 8/2014 | Morris et al. |
| 8,828,225 B2 | 9/2014 | Okafuji et al. |
| 8,836,519 B2 | 9/2014 | Wright et al. |
| 8,845,571 B2 | 9/2014 | Kotanko et al. |
| 8,858,486 B2 | 10/2014 | Zhang et al. |
| 8,858,792 B2 | 10/2014 | Ding et al. |
| 8,864,700 B2 | 10/2014 | Kawamura et al. |
| 8,870,812 B2 | 10/2014 | Alberti et al. |
| 8,881,600 B2 | 11/2014 | Puppini et al. |
| 8,881,915 B2 | 11/2014 | Yokota et al. |
| 8,882,696 B2 | 11/2014 | Tamari |
| 8,882,704 B2 | 11/2014 | Fago et al. |
| 8,883,066 B2 | 11/2014 | Shiki |
| 8,900,173 B2 | 12/2014 | Sugioka |
| 8,905,959 B2 | 12/2014 | Basaglia |
| 8,906,240 B2 | 12/2014 | Crnkovich et al. |
| 8,906,300 B2 | 12/2014 | Wang et al. |
| 8,911,629 B2 | 12/2014 | Tsukamoto |
| 8,924,458 B2 | 12/2014 | Levin et al. |
| 8,926,544 B2 | 1/2015 | Hogard |
| 8,937,553 B2 | 1/2015 | Fujioka et al. |
| 8,950,241 B2 | 2/2015 | Hedmann et al. |
| 8,992,777 B2 | 3/2015 | Doyle |
| 9,005,153 B2 | 4/2015 | Kopperschmidt et al. |
| 9,022,981 B2 | 5/2015 | Oesterreich et al. |
| 9,028,740 B2 | 5/2015 | Gohl et al. |
| 9,033,908 B2 | 5/2015 | Schilthuizen et al. |
| 9,050,411 B2 | 6/2015 | Kelly et al. |
| 9,072,830 B2 | 7/2015 | Kelly et al. |
| 9,072,831 B2 | 7/2015 | Kelly et al. |
| 9,072,843 B2 | 7/2015 | Kelly et al. |
| 9,080,985 B2 | 7/2015 | Stevenson et al. |
| 9,095,661 B2 | 8/2015 | Bene |
| 9,117,012 B2 | 8/2015 | Basaglia |
| 9,119,949 B2 | 9/2015 | Brandl et al. |
| 9,140,251 B2 | 9/2015 | Beiriger |
| 9,155,825 B2 | 10/2015 | Kelly et al. |
| 9,161,980 B2 | 10/2015 | Emnebrant et al. |
| 9,162,020 B2 | 10/2015 | Vantard et al. |
| 9,165,112 B2 | 10/2015 | Doyle et al. |
| 9,173,988 B2 | 11/2015 | Barrett et al. |
| 9,174,172 B2 | 11/2015 | Shiki |
| 9,178,891 B2 | 11/2015 | Wang et al. |
| 9,180,238 B2 | 11/2015 | Bedingfield et al. |
| 9,187,744 B2 | 11/2015 | Merchant |
| 9,189,597 B2 | 11/2015 | Bluemler et al. |
| 9,199,023 B2 | 12/2015 | Takeuchi |
| 9,199,024 B2 | 12/2015 | Sasaki et al. |
| 9,199,205 B2 | 12/2015 | Weber et al. |
| 9,203,143 B2 | 12/2015 | Blumberg, Jr. |
| 9,205,247 B2 | 12/2015 | Ueda et al. |
| 9,208,296 B1 | 12/2015 | Romanick |
| 9,211,369 B2 | 12/2015 | Gartner et al. |
| 9,212,988 B2 | 12/2015 | Akita et al. |
| 9,215,985 B2 | 12/2015 | Gross et al. |
| 9,216,246 B2 | 12/2015 | Kelly et al. |
| 9,220,827 B2 | 12/2015 | Meibaum et al. |
| 9,220,832 B2 | 12/2015 | Weaver et al. |
| 9,226,999 B2 | 1/2016 | Nakel et al. |
| 9,234,302 B2 | 1/2016 | Weber et al. |
| 9,242,035 B2 | 1/2016 | Karoor |
| 9,242,036 B2 | 1/2016 | Bluchel et al. |
| 9,243,625 B2 | 1/2016 | Brandl et al. |
| 9,243,991 B2 | 1/2016 | Wagner et al. |
| 9,250,216 B2 | 2/2016 | Wright et al. |
| 9,254,279 B2 | 2/2016 | Karoor et al. |
| 9,267,500 B2 | 2/2016 | Gronau et al. |
| 9,270,010 B2 | 2/2016 | Blumberg, Jr. |
| 9,272,127 B2 | 3/2016 | Rada et al. |
| 9,278,168 B2 | 3/2016 | Gellman et al. |
| 9,283,246 B2 | 3/2016 | Fenn et al. |
| 9,283,310 B2 | 3/2016 | Royer et al. |
| 9,289,545 B2 | 3/2016 | Olde et al. |
| 9,293,110 B2 | 3/2016 | Dolgos et al. |
| 9,295,394 B2 | 3/2016 | Kopperschmidt et al. |
| 9,295,778 B2 | 3/2016 | Kamen et al. |
| 9,296,611 B2 | 3/2016 | Wong |
| 9,302,037 B2 | 4/2016 | Wilt et al. |
| 9,308,308 B2 | 4/2016 | Ding et al. |
| 9,310,232 B2 | 4/2016 | Heide et al. |
| 9,311,448 B2 | 4/2016 | Gruendken et al. |
| 9,314,207 B2 | 4/2016 | Marterstock |
| 9,314,480 B2 | 4/2016 | Jansson et al. |
| 9,314,560 B2 | 4/2016 | Wiktor |
| 9,320,845 B2 | 4/2016 | Falkenhagen et al. |
| 9,345,827 B2 | 5/2016 | Hertz |
| 9,352,083 B2 | 5/2016 | Heitmeiter et al. |
| 9,352,139 B2 | 5/2016 | Reiter et al. |
| 9,352,283 B2 | 5/2016 | Ying et al. |
| 9,353,220 B2 | 5/2016 | Savariar et al. |
| 9,354,640 B2 | 5/2016 | Byler |
| 9,360,129 B2 | 6/2016 | Smith |
| 9,364,597 B2 | 6/2016 | Wolff et al. |
| 9,364,602 B2 | 6/2016 | Kelly et al. |
| 9,364,604 B2 | 6/2016 | Ferrarini et al. |
| 9,370,614 B2 | 6/2016 | Ahrens |
| 9,375,524 B2 | 6/2016 | Levin et al. |
| 9,383,288 B2 | 7/2016 | Solem et al. |
| 9,387,441 B2 | 7/2016 | Ding et al. |
| 9,399,092 B2 | 7/2016 | Christmann |
| 9,400,199 B2 | 7/2016 | Wolff |
| 9,402,941 B2 | 8/2016 | Rambod et al. |
| 9,402,945 B2 | 8/2016 | Hogard et al. |
| 9,402,987 B2 | 8/2016 | Kamen et al. |
| 9,404,825 B2 | 8/2016 | Katz et al. |
| 9,408,958 B2 | 8/2016 | Wang et al. |
| 9,415,201 B2 | 8/2016 | Marterstock |
| 9,427,513 B2 | 8/2016 | Holmer et al. |
| 9,427,518 B2 | 8/2016 | Brueckner |
| 9,433,356 B2 | 9/2016 | Olde et al. |
| 9,435,459 B2 | 9/2016 | Bedingfield |

(56)                References Cited

U.S. PATENT DOCUMENTS

| | | | |
|---|---|---|---|
| 9,436,802 | B2 | 9/2016 | Romanick |
| 9,440,198 | B2 | 9/2016 | McCloskey et al. |
| 9,442,036 | B2 | 9/2016 | Furmanski et al. |
| 9,452,252 | B2 | 9/2016 | Kopperschmidt |
| 9,463,202 | B2 | 10/2016 | Jansson et al. |
| 9,463,266 | B2 | 10/2016 | Noguchi et al. |
| 9,470,341 | B2 | 10/2016 | Brehm et al. |
| 9,474,846 | B2 | 10/2016 | Steger |
| 9,488,510 | B2 | 11/2016 | Beavis et al. |
| 9,492,794 | B2 | 11/2016 | Yokota et al. |
| 9,504,778 | B2 | 11/2016 | Hopping et al. |
| 9,514,322 | B2 | 12/2016 | Golshenas |
| 9,514,518 | B2 | 12/2016 | Gillespie et al. |
| 9,517,296 | B2 | 12/2016 | Fulkerson et al. |
| 9,518,958 | B2 | 12/2016 | Wilt et al. |
| 9,527,040 | B2 | 12/2016 | Krause et al. |
| 9,527,627 | B2 | 12/2016 | Eyrard et al. |
| 9,542,578 | B2 | 1/2017 | Dattolo et al. |
| 9,545,469 | B2 | 1/2017 | Curtis et al. |
| 9,548,533 | B2 | 1/2017 | Blumberg, Jr. |
| 9,550,021 | B2 | 1/2017 | Beden et al. |
| 9,555,146 | B2 | 1/2017 | Fehr et al. |
| 9,555,181 | B2 | 1/2017 | Hedmann et al. |
| 9,568,432 | B2 | 2/2017 | Baxi et al. |
| 9,582,645 | B2 | 2/2017 | Yu et al. |
| 9,585,992 | B2 | 3/2017 | Bene |
| 9,599,599 | B2 | 3/2017 | Ash et al. |
| 9,612,182 | B2 | 4/2017 | Olde et al. |
| 9,616,160 | B2 | 4/2017 | Daniel |
| 9,616,161 | B2 | 4/2017 | Jansson et al. |
| 9,616,163 | B2 | 4/2017 | Wong et al. |
| 9,616,164 | B2 | 4/2017 | Nuernberger |
| 9,616,393 | B2 | 4/2017 | Hidaka et al. |
| 9,635,111 | B2 | 4/2017 | Wang et al. |
| 9,636,447 | B2 | 5/2017 | Olde et al. |
| 9,642,961 | B2 | 5/2017 | Kelly et al. |
| 9,655,922 | B1 | 5/2017 | Jansson et al. |
| 9,662,485 | B2 | 5/2017 | Chung et al. |
| 9,675,743 | B2 | 6/2017 | Raiford et al. |
| 9,675,745 | B2 | 6/2017 | Kelly et al. |
| 9,682,184 | B2 | 6/2017 | Wong |
| 9,703,926 | B2 | 7/2017 | Dolgos et al. |
| 9,707,329 | B2 | 7/2017 | Merchant et al. |
| 9,713,670 | B2 | 7/2017 | Herrmann et al. |
| 9,724,455 | B2 | 8/2017 | Kopperschmidt et al. |
| 9,742,065 | B2 | 8/2017 | Blumberg, Jr. |
| 9,744,300 | B2 | 8/2017 | Kamen et al. |
| 9,750,865 | B2 | 9/2017 | Vasta et al. |
| 9,752,730 | B2 | 9/2017 | Voelz |
| 9,757,503 | B2 | 9/2017 | Haecker et al. |
| 9,770,546 | B2 | 9/2017 | Vasta |
| 9,775,937 | B2 | 10/2017 | Wang et al. |
| 9,776,143 | B2 | 10/2017 | Krause et al. |
| 9,782,528 | B2 | 10/2017 | Balschat et al. |
| 9,791,270 | B2 | 10/2017 | Paolini et al. |
| 9,795,731 | B2 | 10/2017 | Kelly et al. |
| 9,795,932 | B2 | 10/2017 | Yokota et al. |
| 9,802,162 | B2 | 10/2017 | Hildwein et al. |
| 9,806,399 | B2 | 10/2017 | Blumberg, Jr. |
| 9,808,586 | B2 | 11/2017 | Kogan |
| 9,821,102 | B2 | 11/2017 | Jansson et al. |
| 9,821,106 | B1 | 11/2017 | Vasta et al. |
| 9,821,107 | B2 | 11/2017 | Weaver et al. |
| 9,833,556 | B2 | 12/2017 | Olde et al. |
| 9,836,185 | B2 | 12/2017 | O'Mahony et al. |
| 9,844,620 | B2 | 12/2017 | Stuva et al. |
| 9,846,085 | B2 | 12/2017 | Newell et al. |
| 9,849,228 | B2 | 12/2017 | Noack et al. |
| 9,855,380 | B2 | 1/2018 | Ritter et al. |
| 9,878,086 | B2 | 1/2018 | Kleinekofort |
| 9,883,799 | B2 | 2/2018 | Kotanko et al. |
| 9,889,244 | B2 | 2/2018 | Arrizza et al. |
| 9,901,669 | B2 | 2/2018 | Wolff et al. |
| 9,901,726 | B2 | 2/2018 | Stenzel et al. |
| 9,907,898 | B2 | 3/2018 | Hedmann et al. |
| 9,921,271 | B2 | 3/2018 | Labarthe et al. |
| 9,925,155 | B2 | 3/2018 | Forsback et al. |
| 9,925,320 | B2 | 3/2018 | Childers et al. |
| 9,933,391 | B2 | 4/2018 | Hollstein |
| 9,950,104 | B2 | 4/2018 | Gronau et al. |
| 9,974,895 | B2 | 5/2018 | Storr et al. |
| 9,987,411 | B2 | 6/2018 | Planas et al. |
| 9,993,777 | B2 | 6/2018 | Hayashi et al. |
| 10,002,190 | B2 | 6/2018 | West |
| 10,022,484 | B2 | 7/2018 | Brugger et al. |
| 10,024,442 | B2 | 7/2018 | Maenz et al. |
| 10,044,791 | B2 | 8/2018 | Kamen et al. |
| 10,057,997 | B2 | 8/2018 | Schafer et al. |
| 10,058,692 | B2 | 8/2018 | Geiger et al. |
| 10,080,996 | B2 | 9/2018 | Berzinis et al. |
| 10,099,000 | B2 | 10/2018 | Strohhoefer et al. |
| 10,101,316 | B2 | 10/2018 | Wolff et al. |
| 10,130,749 | B2 | 11/2018 | Schade |
| 10,149,938 | B2 | 12/2018 | Murphy et al. |
| 10,172,990 | B2 | 1/2019 | Stenzel et al. |
| 10,188,991 | B2 | 1/2019 | Menda et al. |
| 10,203,273 | B2 | 2/2019 | Burkert |
| 10,247,663 | B2 | 4/2019 | Janik et al. |
| 10,300,187 | B2 | 5/2019 | Lisitschew |
| 10,307,531 | B2 | 6/2019 | Faulhaber et al. |
| 10,322,220 | B2 | 6/2019 | Riemenschneider |
| 10,391,228 | B2 | 8/2019 | Kelly et al. |
| 2009/0101550 | A1* | 4/2009 | Muller .............. A61M 1/36225 |
| | | | 210/87 |
| 2009/0114037 | A1* | 5/2009 | Smith .................... G01F 1/667 |
| | | | 73/861.28 |

* cited by examiner

FLOWMETER FOR PROPORTIONING WATER IN DIALYSIS SYSTEM

CROSS-REFERENCE TO RELATED APPLICATIONS

The present application claims the benefit of and priority to EP Application No. 20203997.0 filed on Oct. 27, 2020. The entire contents of the foregoing application is incorporated by reference herein.

BACKGROUND

Patients in need of dialysis may be treated using peritoneal dialysis (PD), hemodialysis, and hemofiltration treatments. Peritoneal Dialysis (PD) is a dialysis treatment where a peritoneal dialysis fluid (i.e., dialysate) is cycled into and out of a peritoneal cavity to perform exchange across the peritoneum of the patient. Toxins and metabolic waste products are exchanged between the fluid injected into the peritoneum and the vascularized peritoneal membrane.

Hemodialysis and hemofiltration systems circulate blood and dialysate through a dialyzer having a filter membrane separating blood and dialysate. Toxins and metabolic waste products are exchanged through the dialyzer membrane between the dialysate and the blood circulating through the dialyzer.

These treatments are administered using PD and hemodialysis systems, which may include a controlled flow path for preparing fluids used during a therapy session from water. One or more of the following solutions may be prepared: a peritoneal dialysis fluid, a priming solution, a physiologically compatible solution for contacting blood, a physiologically compatible solution for infusion into a subject, a solution for blood rinse back to a subject, or the like.

Since dialysate is directly introduced into a human body and/or contacts blood through the membrane, dialysate is required to be free of biological and chemical contaminants. The dialysate also needs to contain specific concentrations of solutes and cations for biocompatibility and for performing membrane exchange.

Traditional peritoneal dialysis systems require pre-packaged dialysate, which is expensive due to high manufacturing, shipping, and storage costs. There is a need for peritoneal dialysis systems and hemodialysis systems configured to automatically generate dialysate on demand and other biocompatible solutions to ensure that the generated solutions meet high purity and sterility requirements.

SUMMARY

The present disclosure provides a system for measuring fluid flow in any fluid metering or processing apparatus, such as hemodialysis or peritoneal dialysis systems.

In particular, the system may be used to meter water during preparation of dialysate or any other solutions for use during dialysis from liquid or dry concentrate. The system includes an acoustic flowmeter coupled to a fluid line to measure flow rate through the fluid line from a source of the fluid. The acoustic flowmeter measures time of flight of an ultrasound signal in a flow of fluid to determine the flow rate of the fluid. While very accurate, the acoustic flowmeter may be influenced by the presence of air bubbles in the fluid. The system includes an air bubble trap fluidly coupled to the fluid line upstream of the flowmeter. The terms "fluidly coupled" and "fluidly connected" refer to the ability to pass fluid or gas from one point to another point. The two points can be within or between any one or more of compartments, modules, systems, and components, all of any type.

The air bubble trap is configured to catch and remove bubbles from the fluid before the fluid reaches the flowmeter. The system also includes an air bubble detector and a valve coupled to the fluid line. The air bubble detector is disposed upstream of the flowmeter and downstream of the air bubble trap. The term "downstream" refers to a position of a first component in a flow path relative to a second component wherein fluid passes by the second component prior to the first component during normal operation. Thus, the first component is said to be "downstream" of the second component, while the second component is "upstream" of the first component.

The valve is disposed downstream of the air bubble detector and upstream of the flowmeter. The valve may be a three-way valve configured to control the flow of fluid through the fluid line and a drain line coupled to the fluid line. The valve is controlled by a controller based on a signal from the air bubble detector. In response to bubble detection, namely, a bubble detection signal being above a threshold, the controller switches the fluid flow into the drain line. After the air bubble detection signal drops below the threshold, the controller switches the fluid flow through the fluid line. Thus, the system utilizes the air bubble trap to catch the air bubbles in the fluid, but in the event the air bubbles pass through the air bubble trap, the air bubble detector detects the presence of air and changes the position of the valve to drain a portion of the fluid containing air bubbles.

The system according to the present disclosure reduces errors in the flow rate measurement of the acoustic flowmeter. Error reduction in flowmeter readings, in turn, minimizes and/or eliminates the errors in concentration of the dialysate during its preparation. As noted above, the dialysate may be prepared by reconstituting, i.e., diluting, dialysate concentrate. This may be done by adding water to the concentrate at a flow rate from about 50 ml to about 500 ml per minute.

According to one embodiment of the present disclosure a system for metering fluid in a dialysis device is disclosed. The system includes a fluid source storing a fluid and a fluid line coupled to the fluid source and configured to pass the fluid therethrough. The system also includes a bubble detector coupled to the fluid line downstream of the fluid source, the bubble detector configured to detect bubbles present in the fluid and to generate a bubble detection signal. The system further includes a valve coupled to the fluid line downstream of the fluid source, the valve configured to switch between a first configuration or a second configuration, where in the first configuration the valve is configured to direct the fluid through the fluid line and in the second configuration the valve is configured to direct the fluid through a drain line. The system also includes a controller coupled to the bubble detector and the valve, the controller configured to receive the bubble detection signal and to control the valve based on the bubble detection signal.

Implementations of the above embodiment may include one or more of the following features. The controller may be further configured to perform a comparison of the bubble detection signal to a threshold. The controller may be further configured to determine the presence of at least one air bubble in the fluid based on the bubble detection signal exceeding the threshold. The controller may be further configured to switch the valve to the second configuration in response to the bubble detection signal being above the threshold. The controller may be further configured to switch the valve to the first configuration in response to the bubble detection signal being below the threshold. The system may also include a flowmeter coupled to the fluid line downstream of the valve, the flowmeter configured to measure a flow rate of the fluid and provide a flow rate signal to the controller. The flowmeter may be one of an acoustic flowmeter and/or an optical flowmeter. The system may include a pump coupled to the fluid line and configured move the fluid from the fluid source through the fluid line. The controller may be further configured to control the pump based on the flow rate signal.

According to another embodiment of the present disclosure a system for metering fluid in a dialysis device is disclosed. The system includes a fluid source storing a fluid and a fluid line coupled to the fluid source and configured to pass the fluid therethrough. The system also includes: a bubble detector coupled to the fluid line downstream of the fluid source, the bubble detector configured to detect bubbles present in the fluid and to generate a bubble detection signal; and a valve coupled to the fluid line downstream of the fluid source, the valve configured to switch between a first configuration or a second configuration, where in the first configuration the valve is configured to direct the fluid through the fluid line and in the second configuration the valve is configured to direct the fluid through a drain line. The system further includes a controller coupled to the bubble detector and the valve. The controller is configured to: receive the bubble detection signal; switch the valve to the first configuration in response to the bubble detection signal being below a threshold indicative of a presence of the bubbles in the fluid; and switch the valve to the second configuration in response to the bubble detection signal being above the threshold indicative of the presence of the bubbles in the fluid.

Implementations of the above embodiment may include one or more of the following features. The system may include a flowmeter coupled to the fluid line downstream of the valve, the flowmeter configured to measure a flow rate of the fluid and provide a flow rate signal to the controller. The flowmeter may be an acoustic flowmeter and/or an optical flowmeter. The system may include a pump coupled to the fluid line and configured move the fluid from the fluid source through the fluid line. The controller may be further configured to control the pump based on the flow rate signal.

According to a further embodiment of the present disclosure a method for metering fluid in a dialysis device is disclosed. The method includes supplying a fluid from a fluid source to a fluid line coupled to the fluid source and detecting bubbles present in the fluid at a bubble detector coupled to the fluid line downstream of the fluid source. The method also includes transmitting a bubble detection signal from the bubble detector to a controller. The method further includes controlling a valve coupled to the fluid line downstream of the fluid source by the controller. Controlling the valve also includes: switching a valve to a first configuration, in which the valve is configured to direct the fluid through the fluid line, in response to the bubble detection signal being below a threshold indicative of a presence of the bubbles in the fluid; and switching the valve to a second configuration, in which the valve is configured to direct the fluid through a drain line, in response to the bubble detection signal being above the threshold indicative of the presence of the bubbles in the fluid.

Implementations of the above embodiment may include one or more of the following features. The method may include measuring a flow rate of the fluid at a flowmeter coupled to the fluid line downstream of the valve. The method may also include transmitting a flow rate signal from the flowmeter to the controller. The flowmeter may be an acoustic flowmeter and/or an optical flowmeter. The method may further include pumping the fluid from the fluid source through the fluid line via a pump coupled to the fluid line. The method may also include controlling the pump based on the flow rate signal.

BRIEF DESCRIPTION OF THE DRAWINGS

Embodiments of the present disclosure are described herein with reference to the accompanying drawings, wherein.

DETAILED DESCRIPTION

Figure 1:
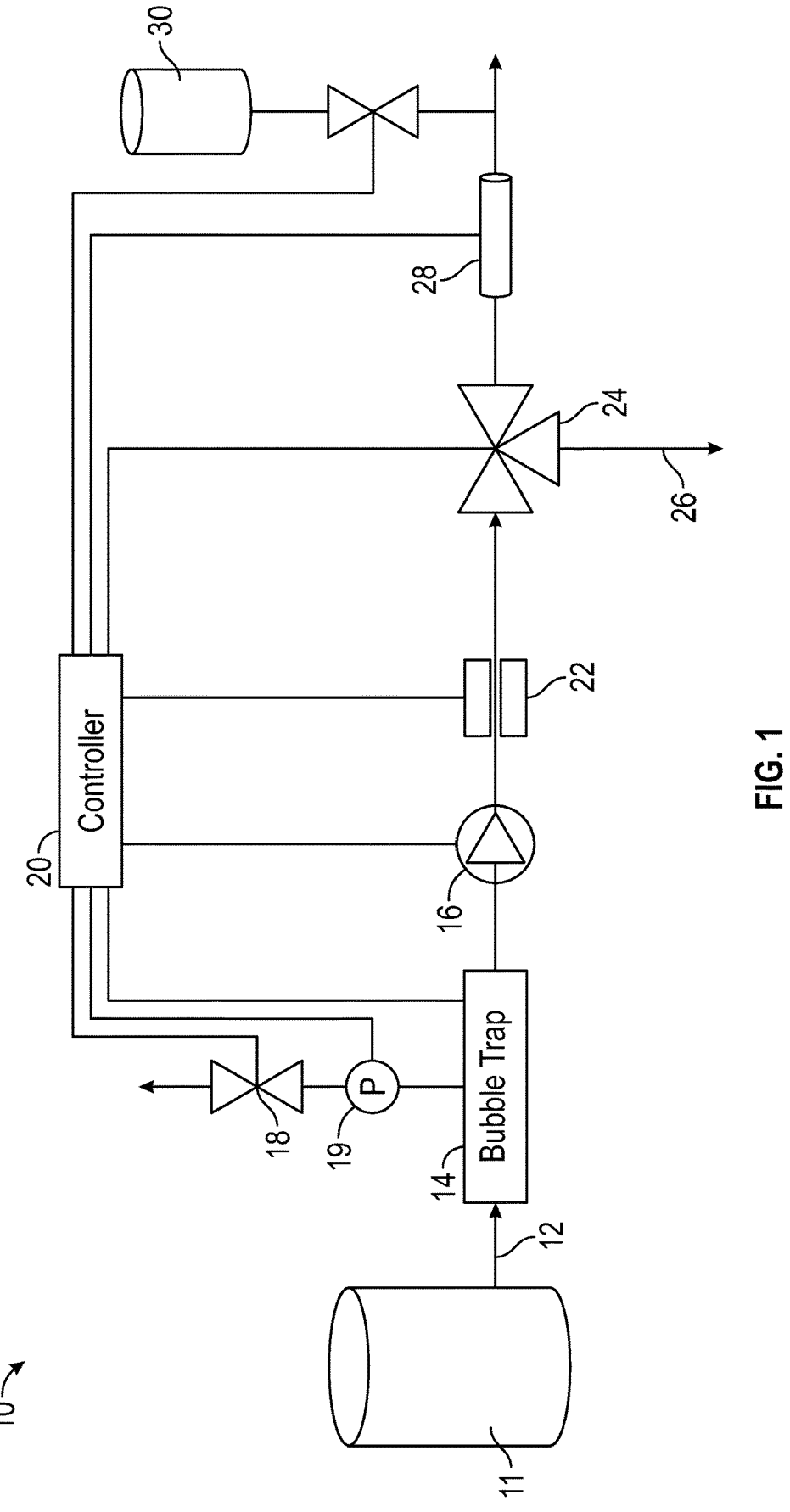
FIG. 1 is a schematic diagram of a system for generating a physiological fluid according to the present disclosure.

With reference to FIG. 1, a system 10 for generating a physiological solution, such as peritoneal dialysis fluid is shown. The system includes a fluid source 11, such as a water tank. Fluid is pumped from fluid source 11 into a fluid line 12 using a pump 16 through a bubble trap 14. The pump 16 is disposed downstream of the fluid source 11 and may be any suitable pump for pumping fluid such as a gear pump, a piston pump, and the like. The pump 16 may be disposed downstream or upstream of the bubble trap 14. The bubble trap 14 may be any bifurcated chamber configured to separate air and water. The bubble trap 14 may be coupled to an optional venting valve 18 configured to vent air from the bubble trap 14. The bubble trap 14 may also include an optional pressure sensor 19 configured measure pressure within the bubble trap 14. The venting valve 18 and the pressure sensor 19 may be replaced by a mechanical vent.

The system 10 also includes a controller 20 coupled to the venting valve 18 and the pressure sensor 19. The controller 20 is configured to receive pressure measurements from the pressure sensor 19 and to control the venting valve 18 based on the feedback from the pressure sensor 19. The controller 20 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein. In embodiments, the controller may include discrete electronic components, full analogic components, non-microcontroller or digital components.

The controller 20 is coupled to the pump 16 and is configured to control the flow rate at which the pump 16 is operated. The controller 20 is also coupled to other components of the system 10 and is configured to receive input from various sensors and control valves and other flow control devices.

The system 10 further includes a bubble detector 22 on the fluid line 12 disposed downstream of the bubble trap 14 and the pump 16. The bubble detector 22 may be an acoustic and/or an optical bubble detector. The bubble detector 22 is configured to detect the presence of air bubbles in the fluid based on disruption in the acoustic and/or optical signals transmitted through the fluid line 12. The bubble detector 22 is coupled to the controller 20 and is configured to provide a measurement signal to the controller 20 indicating the presence of air bubbles in the fluid flowing the fluid line 12.

A drain valve 24 is disposed downstream of the bubble detector 22 on the fluid line 12. In embodiments, the drain valve 24 may be replaced by a plurality of electronic valves or any other suitable combination of flow control devices to avoid introducing air into the fluid line 12. The drain valve 24 may be a three-way solenoid valve controllable by the controller 20. The drain valve 24 is configured to operate in a first configuration, in which the fluid flows through the fluid line 12 and in a second configuration, in which the fluid flows to a drain line 26.

The system 10 also includes a flowmeter 28, which may be an acoustic and/or an optical flowmeter, or any other meter susceptible to air bubbles present in the fluid, which would affect the accuracy of the flowmeter 28. The flowmeter 28 is coupled to the controller 20 and is configured to provide the controller 20 with a signal indicative of the flow rate through the fluid line 12. The controller 20 is configured to control the pump 16 based on the measured flow rate to meter the fluid supplied from the fluid source 11. The fluid may be supplied downstream to be mixed with a dialysate concentrate supplied from a concentrate source 30 to form dialysate. In embodiments, the fluid may be used to mix any other suitable physiological solution for use during dialysis, e.g., peritoneal dialysis or hemodialysis.

Figure 2:
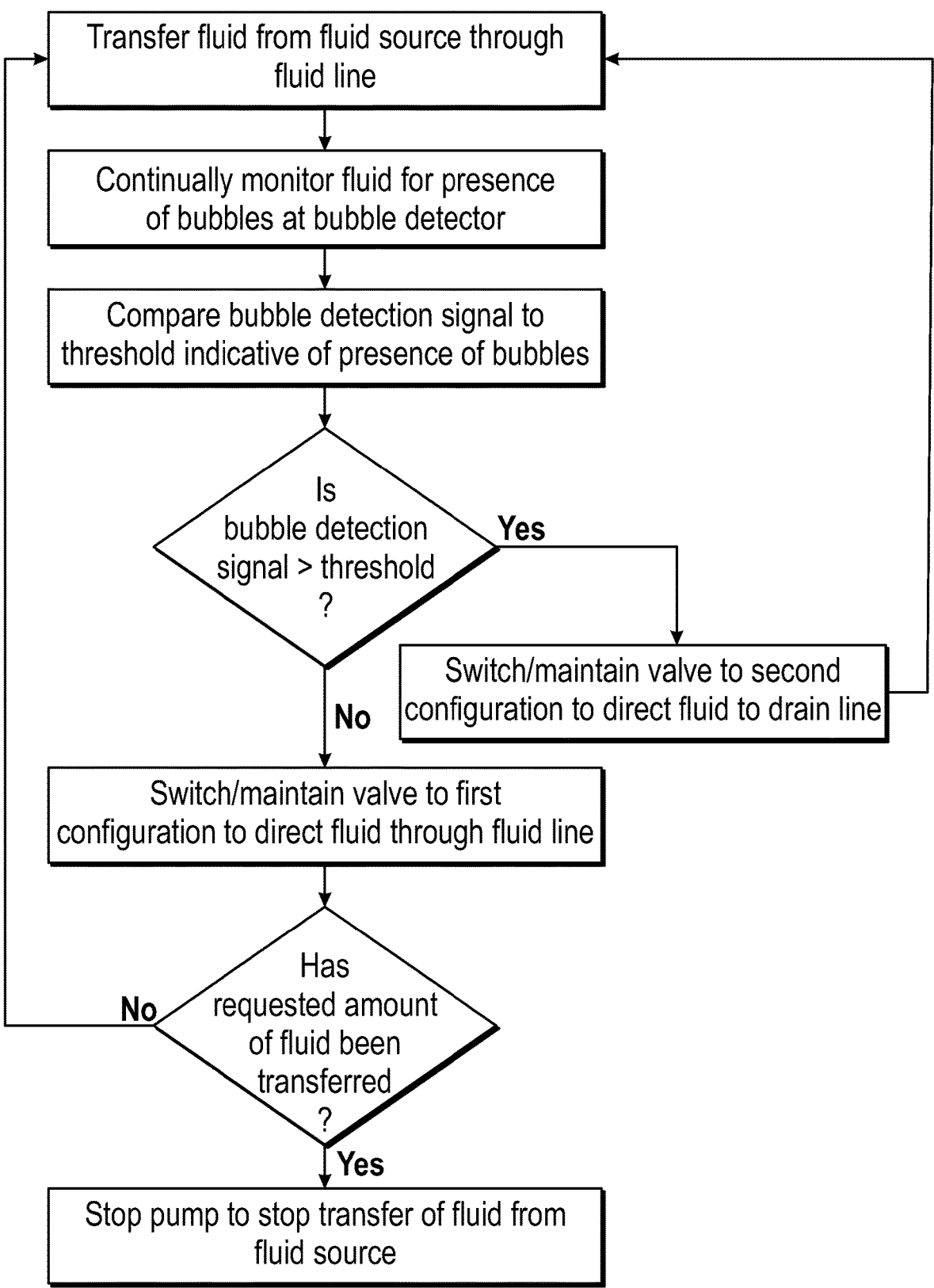
FIG. 2 is a method of operating the system of FIG. 1 according to the present disclosure.

With reference to FIG. 2, a method for controlling the system 10 commences with a command supplied to the controller 20 for metering the fluid from the fluid source 11. This may be done in response to a treatment initialization command supplied to the controller 20 from a main controller (not shown). The command may include a total amount of fluid to be supplied from the fluid source 11. The controller 20 calculates the flow rate for achieving the requested amount of fluid and sets the pump 16 to operate at the calculated flow rate. Once the pump 16 is activated, the fluid flow commences and the fluid flows through the bubble trap 14 and subsequently through the bubble detector 22. The bubble detector 22 continuously monitors the fluid for bubbles, e.g., every 1 millisecond, and provides the signal to the controller 20. The controller 20 compares the bubble detection signal from the bubble detector 22 to a threshold to determine if there are air bubbles present in the fluid. If the controller 20 detects that air bubbles are present based on the bubble detection signal exceeding the threshold, the controller 20 signals the drain valve 24 to switch to the second configuration to allow the fluid to flow to the drain line 26. The drain valve 24 is maintained in the second configuration until the controller 20 determines that the fluid no longer has any air bubbles. The bubble detector 22 continues to transmit the bubble detection signal to the controller 20. If the controller 20 determines that the signal drops below the threshold indicating that there are no bubbles present in the fluid, the controller 20 signals the drain valve 24 to switch into the first configuration, in which the drain valve 24 allows the fluid to flow through the fluid line 12. The controller 20 continues to operate the pump 16 until the requested amount of fluid has been metered by the pump 16, which is calculated by the controller 20 based on the flow rate signal supplied by the flowmeter 28.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques).

What is claimed is:

1. A system for metering fluid in a dialysis device comprising:
   a fluid source storing a fluid;
   a fluid line coupled to the fluid source and configured to pass the fluid therethrough;
   a bubble detector coupled to the fluid line downstream of the fluid source, the bubble detector configured to detect bubbles present in the fluid and to generate a bubble detection signal;
   a bubble trap coupled to the fluid line between the bubble detector and the fluid source,
      wherein the bubble trap is configured to separate gas and liquid;
   a valve coupled to the fluid line downstream of the bubble detector and bubble trap, the valve configured to switch between a first configuration and a second configuration, wherein in the first configuration the valve directs the fluid through the fluid line and in the second configuration the valve directs the fluid through a drain line;
   a controller coupled to the bubble detector and the valve, the controller configured to receive the bubble detection signal and to control the valve based on the bubble detection signal;
   a flowmeter coupled to the fluid line downstream of the valve, the flowmeter configured to measure a flow rate of the fluid based on an ultrasound signal and provide a flow rate signal to the controller;
   a concentrate source downstream from the flowmeter and configured to contain a dialysate concentrate for mixing with the fluid to produce peritoneal dialysate fluid; and
   a pump coupled to the fluid line and configured to move the fluid from the fluid source through the fluid line, wherein the controller is configured to control the pump based on the flow rate signal.

2. The system according to claim 1, wherein the controller is further configured to perform a comparison of the bubble detection signal to a threshold.

3. The system according to claim 2, wherein the controller is further configured to determine presence of at least one air bubble in the fluid based on the bubble detection signal exceeding the threshold.

4. The system according to claim 2, wherein the controller is further configured to switch the valve to the second configuration in response to the bubble detection signal being above the threshold.

5. The system according to claim 2, wherein the controller is further configured to switch the valve to the first configuration in response to the bubble detection signal being below the threshold.

6. The system according to claim 1, wherein the flowmeter is an acoustic flowmeter.

7. The system according to claim 1, the system further comprising:
   a venting valve configured to vent air from the bubble trap.

8. The system according to claim 1, wherein the bubble trap includes a pressure sensor configured to measure pressure within the bubble trap.

9. A system for metering fluid in a dialysis device comprising:

a fluid source storing a fluid;

a fluid line coupled to the fluid source and configured to pass the fluid therethrough;

a bubble detector coupled to the fluid line downstream of the fluid source, the bubble detector configured to detect bubbles present in the fluid and to generate a bubble detection signal;

a bubble trap coupled to the fluid line between the bubble detector and the fluid source, wherein the bubble trap is configured to separate gas and liquid;

a valve coupled to the fluid line downstream of the bubble detector and bubble trap, the valve configured to switch between a first configuration and a second configuration, wherein in the first configuration the valve directs the fluid through the fluid line and in the second configuration the valve directs the fluid through a drain line;

a controller coupled to the bubble detector and the valve, the controller configured to:

receive the bubble detection signal;

switch the valve to the first configuration in response to the bubble detection signal being below a threshold indicative of a presence of the bubbles in the fluid; and

8 switch the valve to the second configuration in response to the bubble detection signal being above the threshold indicative of the presence of the bubbles in the fluid;

a flowmeter coupled to the fluid line downstream of the valve, the flowmeter configured to measure a flow rate of the fluid based on an ultrasound signal and provide a flow rate signal to the controller;

a concentrate source downstream from the flowmeter and configured to contain a dialysate concentrate for mixing with the fluid to produce peritoneal dialysate fluid; and a pump coupled to the fluid line and configured to move the fluid from the fluid source through the fluid line, wherein the controller is configured to control the pump based on the flow rate signal.

10. The system according to claim 9, wherein the flowmeter is an acoustic flowmeter.

11. The system according to claim 9, further comprising a pump coupled to the fluid line and configured move the fluid from the fluid source through the fluid line.

12. The system according to claim 9, the system further comprising:

a venting valve configured to vent air from the bubble trap.

13. The system according to claim 9, wherein the bubble trap includes a pressure sensor configured to measure pressure within the bubble trap.

* * * * *